United States Patent [19]

Hayakawa et al.

[11] Patent Number: 5,800,390
[45] Date of Patent: Sep. 1, 1998

[54] EQUIPMENT FOR INTRACEREBRAL ADMINISTRATION OF PREPARATIONS

[75] Inventors: Toru Hayakawa, Kobe; Toshiki Yoshimine, Ashiya; Hiromu Yamamoto, Higashitagawa-gun; Akira Sato, Tsuruoka; Tsunemasa Irie, Takarazuka; Keiji Fujioka, Amagasaki; Yoshihiro Takada, Suita; Yoshio Sasaki, Takatsuki, all of Japan

[73] Assignees: Sumitomo Pharmaceuticals Company, Limited, Osaka; Koken Co., Ltd., Tokyo, both of Japan

[21] Appl. No.: 900,135

[22] PCT Filed: May 22, 1992

[86] PCT No.: PCT/JP92/00658

§ 371 Date: Nov. 24, 1993

§ 102(e) Date: Nov. 24, 1993

[87] PCT Pub. No.: WO92/20400

PCT Pub. Date: Nov. 26, 1992

Related U.S. Application Data

[63] Continuation of Ser. No. 533,355, Sep. 25, 1995, abandoned, which is a continuation of Ser. No. 142,392, Nov. 24, 1993, abandoned.

[30] Foreign Application Priority Data

May 24, 1991 [JP] Japan ................................ 3-120115

[51] Int. Cl.$^6$ .................................................. A61M 11/00
[52] U.S. Cl. .................... 604/93; 604/60; 604/891.1; 424/423
[58] Field of Search ................ 604/891.1, 890.1, 604/9, 51, 60, 64, 72, 93, 164, 167, 218, 233, 235, 264, 116, 117, 285, 411; 128/769, 772; 424/423, 424

[56] References Cited

U.S. PATENT DOCUMENTS

| Re. 34,416 | 10/1993 | Lemieux | 604/164 |
| 4,249,541 | 2/1981 | Pratt | 128/753 |

(List continued on next page.)

FOREIGN PATENT DOCUMENTS

| 0223763 | 5/1987 | European Pat. Off. . | |
| 0233986 | 9/1987 | European Pat. Off. . | |
| 0255123 | 2/1988 | European Pat. Off. | 604/187 |
| 255123 | 5/1988 | European Pat. Off. . | |
| 03 32943A1 | 9/1989 | European Pat. Off. . | |
| 0332943 | 9/1989 | European Pat. Off. . | |
| 412554 | 11/1994 | European Pat. Off. . | |
| 89/04655 | 6/1989 | WIPO . | |

*Primary Examiner*—Michael Buiz
*Assistant Examiner*—A. T. Nguyen
*Attorney, Agent, or Firm*—Birch, Stewart, Kolasch & Birch, LLP

[57] ABSTRACT

Equipment for intracerebral administration of preparations is composed of a preparation-administering device (1) holding a preparation (2), and a plunger (4) removably arranged in the preparation-administering device adapted to push the preparation held therein toward one end of the preparation-administering device. The intracerebral preparation-administration equipment is inserted into a preparation-introducing guide (5) previously implanted in the head of a patient to introduce the preparation into its guide hole (26). The preparation is then guided to a site of administration through a flexible guide tube (23) communicated with the guide hole of the preparation-introducing guide. The equipment for intracerebral administration of preparations may be composed of a tubular preparation-retaining member (30) having a preparation contained therein, and a holder (32) for holding the tubular preparation-retaining member along with a push rod (31) inserted thereinto as an integral part thereof. In this case, the administration equipment itself is inserted into and held in the preparation-introducing guide (5).

19 Claims, 5 Drawing Sheets

U.S. PATENT DOCUMENTS

| | | | |
|---|---|---|---|
| 4,317,445 | 3/1982 | Robinson | 604/264 X |
| 4,693,257 | 9/1987 | Markham | 128/752 |
| 4,767,400 | 8/1988 | Miller et al. | |
| 4,817,631 | 4/1989 | Schnepp-Pesch et al. | 128/753 |
| 4,820,267 | 4/1989 | Harman | 604/60 |
| 4,863,431 | 9/1989 | Vaillancourt | 604/168 |
| 4,877,037 | 10/1989 | Ko et al. | 128/756 |
| 4,941,874 | 7/1990 | Sandow et al. | |
| 4,950,234 | 8/1990 | Fujioka et al. | |
| 4,961,729 | 10/1990 | Vaillancourt | 604/164 |
| 5,098,395 | 3/1992 | Fields | 604/168 |

EQUIPMENT FOR INTRACEREBRAL ADMINISTRATION OF PREPARATIONS

This application is a continuation application under 37 C.F.R. §1.62 of prior application Ser. No. 08/533,355, filed on Sep. 25, 1995, now abandoned, which is a continuation application under 37 C.F.R. §1.62 of prior application Ser. No. 08/142,392, filed on Nov. 24, 1993, now abandoned.

TECHNICAL FIELD

The present invention relates to equipment for intracerebral administration of preparations and, more particularly, an intracerebral preparation-administering equipment for use in the medical field to administer a preparation containing one or more drugs directly to internal part of the brain to carry out medical treatment of the brain.

BACKGROUND ART

As is well known, functions of the living body are controlled by bioactive substances which are produced in a certain part of the living body and brought their ability into full play at that part. Similarly, even in the brain, the living body produces bioactive substances required to control activities of the brain. Among them, there has been known such a bioactive substance, so-called nerve growth factor. This bioactive substance is a neurotrophic factor having a function to cause the cell respiration and cell differentiation of the brain and is a protein on which people place their hopes as a material for development of a new medicine for senile dementias, which are becoming a problem recently, for example, nervous degenerated diseases such as Alzheimer's disease, i.e., one of dementia presenilis.

As a means for carrying out administration of preparations containing the above bioactive substance, it would be thought of using oral administration or intravenous administration. In case of the oral administration of bioactive substances, however, it provides almost no drug efficacy because of decomposition in the digestive system or a first-pass effect caused at the liver. On the other hand, in case of the intravenous administration, it is difficult to transfer the drug to the internal part of the brain as the blood brain barriers could be a large obstacle in passage of the drug. That is, most of the substances can not pass through blood brain barriers as blood capillaries in the substantive parts of the brain have inner walls covered with cells which are poor in permeability and have such a unique structure that these inner cells are joined together by tight junctions. In addition, the blood brain barriers, which are present between the brain and the blood in the brain, prevent disordered transfer or distribution of ingredients of the blood or medicines administered to or absorbed in the blood. Thus, there is such a problem that proteinaceous bioactive substances such as the nervous growth factor can not be transferred to the brain by the general oral administration or intravenous administration.

Aa a solution to these problems it would be thought of (1) administration of a bioactive substance to the spinal cord, or (2) administration of a bioactive substance to the brain by craniotomy or transforation. However, the process (1) is unsuitable for administration of bioactive substances as braincerebrospinal barrier prevents disordered transfer or distribution of high polymers such as protein, peptide and the like in the same manner as the blood brain barriers. On the other hand, the process (2) has such problems that it requires surgical operations, that it is complex in handling, and that it would make physical, psychological and economical burdens too heavy for the patient. Further, there is a great risk of occurrence of infectious diseases. In addition, it is necessary to administer the bioactive substances at frequent intervals to improve the curative effect since the bioactive substances are short in half-life time even if administered to the internal part of the brain directly.

The problem that the repeated administration is required would be solved to a certain extent by use of a sustained release preparation, which has been proposed in Japanese patent application Ser. No. 1-208484 by some of the present inventors to extend the duration time of the bioactive substances. However, there still remains a problem of how to administer the preparations to the internal part of the brain without surgical operations.

Separate from the above, as the most sure means for sending a preparation into the brain, there has been known an Ommaya reservoir by which a catheter is left in the cerebral ventricle. Although this reservoir makes it possible to administer a preparation to the internal part of the brain, it is impossible to supply the preparations continuously. In addition, it cannot be applied to preparations other than liquid-like preparations. Thus, this reservoir is not suitable for administration of the preparations containing bioactive substances as the preparation requires repeated administration because of a short half-life time thereof.

DISCLOSURE OF INVENTION

Accordingly, the present invention intends to make it easy to handle an equipment as well as to make it possible to administer preparations repeatedly to a site of administration in a certain internal part of the brain.

According to the present invention, the above object is achieved by providing equipment for intracerebral administration of preparations, which comprises: preparation-administering means containing a preparation; and a plunger removably arranged in said preparation-administrating means for pushing the preparation out of said preparation-administering means toward one end thereof, said equipment being adapted to be used in combination with a preparation-introducing guide previously implanted in the head of a patient.

In a preferred embodiment of the present invention, the preparation-introducing guide is composed of a guide body having a guide holes for introducing a preparation, and a flexible guide tube connected to a lower end of the guide body so as to communicate with the guide hole, for introducing the preparation introduced into the guide hole to the site of application.

The above guide body has a guide hole comprising a tapered introducing part and a cylindrical part communicated therewith, and is provided with an elastic member press-fitted in the cylindrical part of the guide hole to prevent backflow by closing the guide hole, and a cylindrical pressure member having a tapered guide hole and being fitted in said guide hole of the guide body to fix the elastic member in place.

In another preferred embodiment, the preparation-administering means is made in the form of a hollow needle structure. In this case, the preparation-administrating means may be made in the form of a double needle structure composed of a hollow outer needle, and an inner needle removably arranged in the outer needle.

In another preferred embodiment, in order to allow the preparation-administrating means to hold a preparation, the preparation-administering equipment is provided with a preparation-holder composed of a preparation-holder body containing a preparation, and a plunger removably arranged therein, the preparation-holder being removably attached to the outer needle of the preparation-administrating means, whereby the preparation in the preparationholder body is pushed in the outer needle by means of the plunger.

Further, according to the present invention, the above object is achieved by providing an equipment for intracerebral administration of preparations, to be used in combination with a preparation-introducing guide having a flexible guide tube for introducing a preparation loaded in a preparation-introducing guide hole to a site of application in an internal part of the brain, said equipment comprising a tubular preparation-retaining member including a preparation and being movable within the flexible guide tube of said preparation-introducing guide; and a preparation-retaining member holder capable of being inserted in a guide hole of said preparation-introducing guide.

In a preferred embodiment, the preparation-administering equipment includes a needle member for introducing the preparation-retaining member into the preparation-introducing guide. Although this needle member may be constituted only by a cylindrical member having such an inside diameter that the preparation-retaining member holder may pass therethrough, it is preferred to constitute the needle member with a hollow outer needle having an inside diameter through which the preparation-retaining member holder may be passed, and an inner needle removably attached to the outer needle adapted to be fitted in the guide hole of the preparation-introducing guide to determine its position.

As the preparations suitable for administration by the intracerebral preparation-administrating equipment of the present invention, there are given those such as sustained release, solid preparations and semi-solid preparations. The solid preparations may be divided, by the kind of a carrier ingredient thereof, into two groups, i.e., biodegradable solid preparations and non-biodegradable solid preparations. The biodegradable solid preparations include sustained release preparations containing a carrier such as collagen, gelatin, albumin, polylactic acid, polyglycolic acid, lactic acid-glycolic acid copolymer, chitin, chitosan, etc. On the other hand, the non-biodegradable solid preparations include a carrier such as silicone, and vinyl copolymers. However, the carriers of these preparations are never limited to the above materials. Further, the semi-solid preparations includes gel-like semi-solid preparations.

If there is no need to take out the preparation after use because of its disintegration, dissolution, or decomposition in the internal part of the brain, the administration may be carried out by inserting the needle-like member of the intracerebral preparation-administering equipment into the preparation-introducing guide previously implanted in the head so that a distal end of the guide is positioned at a site of administration, loading a preparation into the needle-like member, and then operating the intracerebral preparation-administrating equipment. In this case, the preparation is introduced into and surely administered to the site of administration through the needle-like member and the preparation-introducing guide.

On the other hand, in case of that the preparation has to be taken out of the brain after administration because of the fact that disintegration, dissolution or decomposition of the preparation doesn't take place in the internal part of the brain, the intracerebral preparation-administering equipment is preferably constituted by a tubular preparation-retaining member, a push rod inserted in the preparation-retaining member to hold a preparation therein on the side of one end of the preparation-retaining member, and a holder for integrally holding the preparation-retaining member along with the push rod inserted therein. In this case, the push rod constituting the intracerebral preparation-administering equipment may be omitted therefrom. By introducing the intracerebral preparation-administering equipment into the preparation-introducing guide implanted in the head of the patient and leaving it as it is, the preparation in the distal end of the preparation-retaining member is administered to the side of a certain administration. The repeated administration can be performed by taking the intracerebral preparation-administering equipment out of the preparation-introducing guide after a certain time or a certain period of time has been elapsed, and then loading another new intracerebral preparation-administering equipment into the preparation-introducing guide. In this base, it is possible to fill up the tubular preparation-retaining member with a semi-solid preparation as well as to obtain semipermanent curative effects, provided that the tubular preparation-retaining member is charged with a substance producing or secreting medicine, or bioactive substances effective for medical treatment of the internal part of the brain, for example, a certain kind of cells.

Further scope of applicability of the present invention will become apparent from the detailed description given hereinafter. However, it should be understood that the detailed description and specific example, while indicating preferred embodiments of the invention, are given by way of illustration only, since various changes and modifications within the spirit and scope of the invention will become apparent to those skilled in the art from this detailed description.

BRIEF DESCRIPTION OF DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

The present invention will be explained below in detail, making reference to the accompanying drawings illustrating embodiments thereof.

Figure 1A:
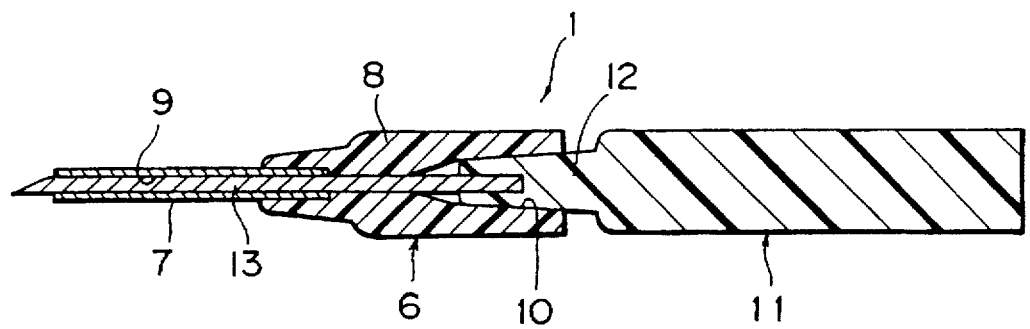
FIGS. 1(a), 1(b), 1(c) and 1(d) are sectional views of a set of an intracerebral preparation-administering equipment and a preparation-introducing guide according to the present invention.

An intracerebral preparation-administering equipment according to the present invention, shown in FIGS. 1(a)–1

(d) is suitable for administration of such preparations that they disintegrate, or dissolve or decompose in the internal part of the brain and require no removal of the residue. This intracerebral preparation administering equipment comprises a double needle 1 serving as a preparation-administrating means, a preparation holder 3 having a preparation 2 contained therein, and a plunger 4 for pushing out the preparation 2 loaded in the double needle 1 to a site of administration. The equipment is used in combination with a preparation-introducing guide 5.

The double needle 1 comprises an outer needle 6 and an inner needle 11. The outer needle 6 is composed of a cannula 7 of a stainless steel or any other material, and a cylindrical holding member 8 for holding the cannula. The cylindrical holding member 8 is made of a plastic material with good biocompatibility, for example, silicone, and provided with a tapered fitting hole 10 communicating with a hole 9 of the cannula 7. The inner needle 11 has a tapered projection 12 adapted to be inserted removably into the fitting hole 10 of the outer needle 6, the projection 12 is provided with a solid insertion needle 13 with a sharp pointed end. The insertion needle 13 is of a stainless steel or any other suitable material and is so designed as to have a length such that it protrudes beyond the distal end of the cannula 7 when the inner needle 11 is inserted into the outer needle 6 completely.

The preparation holder 3 is composed of a cylindrical body 15 with a tapered projection 14, and a plunger 17 produced in the form of an arrow feather and provided at one end thereof with a push rod 16. The preparation holder 3 is so designed that the preparation 2 put in the holder body 15 is loaded into the preparation-introducing guide 5 by removably inserting the projection 14 into the fitting hole 10 of the outer needle 6.

The plunger 4 is composed of a flexible rod 18 and a plunger handle 19. The plunger is so designed that it thrusts the preparation 2 to the site of administration when the flexible rod 18 is inserted into the outer needle 6 in use. The flexible rod 18 is required to have a flexibility as well as the guide tube, though there is no limitation of the material therefor. Typical materials for the flexible rod are polymers such as, for example, polyvinyl chloride, poly-propylene, nylon 12, and Teflon (Trademark of Du Pont), and stainless steels such as SUS 316.

The preparation-introducing guide 5 comprises a guide body 20 of silicone, an elastic backflow check member 21, a cylindrical pressure member 22, and a flexible guide tube 23. The guide body 20 is made of silicone or other material with good biocompatibility and has a tapered guide hole 20a and a cylindrical guide hole 20b communicated therewith. Fitted in the cylindrical guide hole is a guide member 24, which is made of silicone or other plastic material with a good biocompatibility, or a stainless steel. The guide member 24 provides a cylindrical recess 25 and a funnel-like guide hole 26 joined thereto, the cylindrical recess 25 being joined to the tapered guide hole 20a of the guide body 20. The elastic backflow check member 21, which has a diameter slightly greater than that of the cylindrical recess 25, is press-fitted in cylindrical recess 25 and fixed under pressure by the cylindrical pressure member 22 to close the guide hole 26 opened at the bottom of the cylindrical recess 25. The cylindrical pressure member 22 is made of an elastic material, for example, silicone rubber.

Further, the cylindrical pressure member 22 has a trumpet-shaped guide hole 27 so as to align the cannula 7 of the double needle with the guide hole 26. The flexible guide tube 23 is attached coaxially with the guide hole 26 of the guide member 24 to a tapered projection 28 protruding downward from the guide body 20 and communicated with the funnel-shaped guide hole 26. The flexible guide tube 23 is formed of a plastic material with a good biocompatibility, such as silicone.

Figure 2:
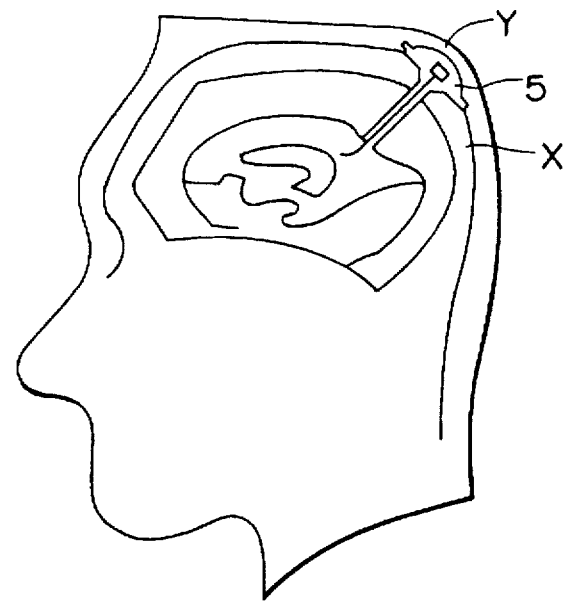
FIG. 2 is an explanatory diagram illustrating the state of the preparation-introducing guide of FIG. 1 that is being implanted in the head.

Prior to use of the intracerebral preparation-administering equipment of the above structure, the preparation-introducing guide 25 is fixed in the head X of a patient by surgical operation, as shown in FIG. 2. At that time, the distal end of the guide tube 23 of the preparation-introducing guide 5 is fixed to the site to which the preparation 2 is administered, i.e., the site of application, while the guide body 20 is fixed on the skull X but under the scalp Y. Thus, the guide body is marked by the external appearance of a slight swelling on the scalp.

Further, the provision of dot lines on the external surface of the guide tube 23 makes it possible to ascertain the facts that the preparation-introducing guide is properly located in the site of administration by taking X-ray photographs after or at the time of implantation of the preparation-introducing guide.

Figure 1B:
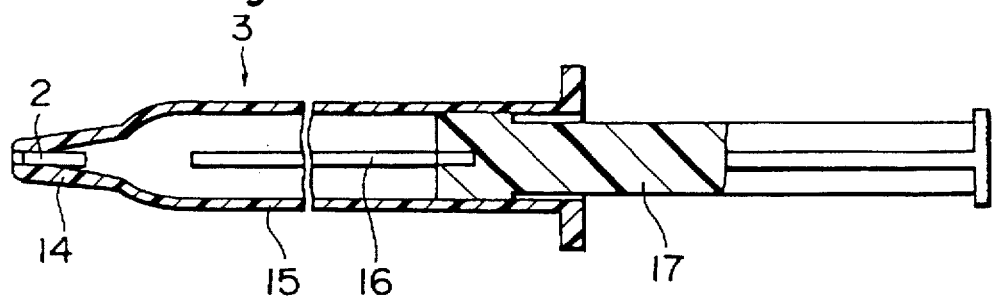
Figure 1C:
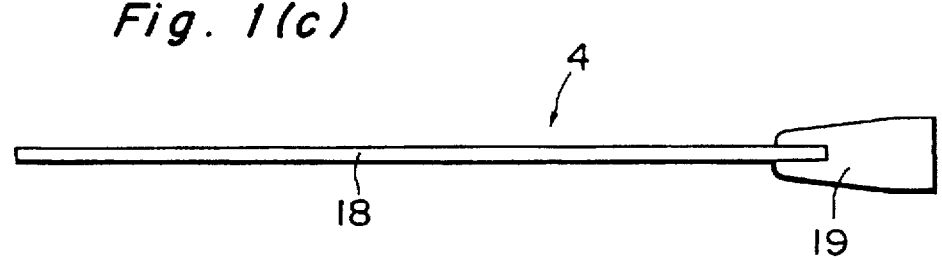
Figure 1D:
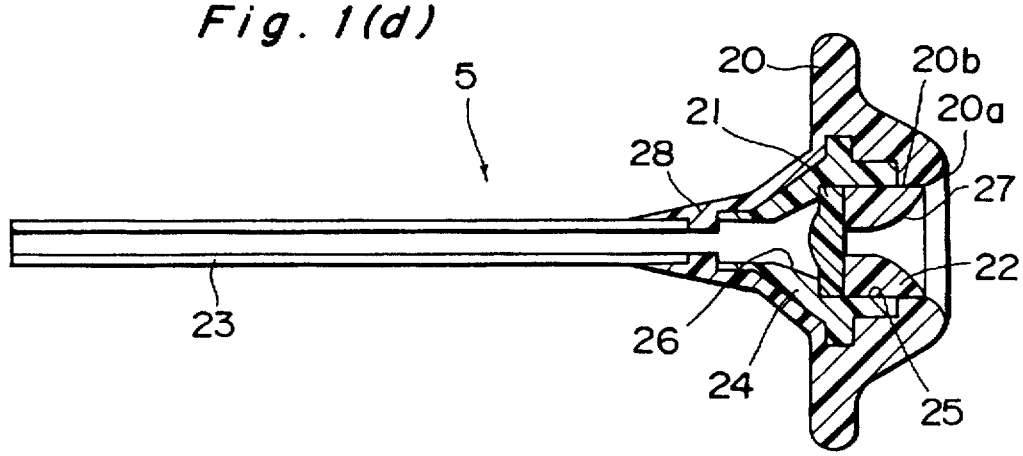
Figure 3A:
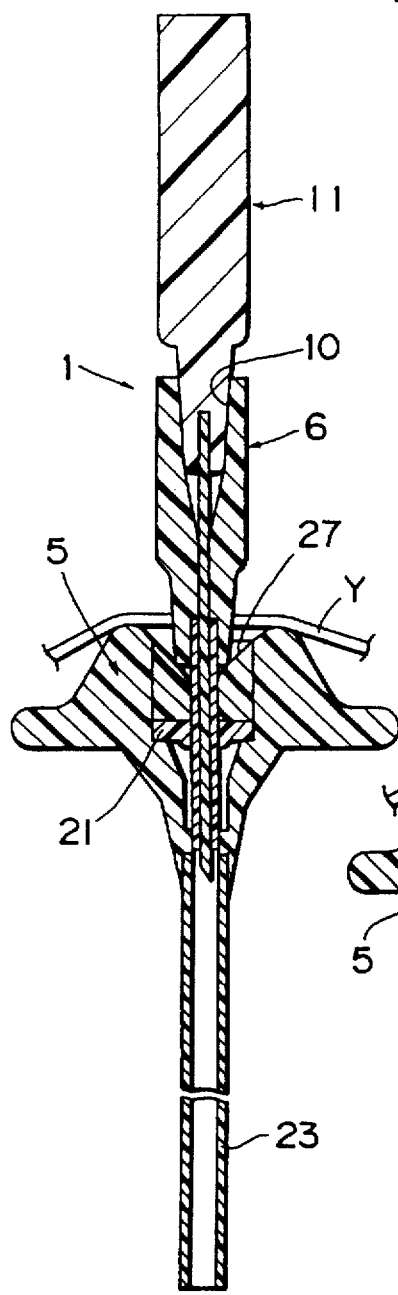
FIGS. 3(a), 3(b) and 3(c) are explanatory diagrams illustrating the condition of the intracerebral preparation-administering equipment of FIG. 1 that is in use.

When making use of the above intracerebral preparation-administering equipment, firstly, the double needle 1 is pushed into the introducing guide 5 through the scalp Y as shown in FIG. 3(a), whereby the distal end of the double needle 1 is guided towards the elastic backflow check member 21 through the guide hole 27 of the preparation-introducing guide 5 and passed through the elastic backflow check member 21 by further pushing the double needle 1. After pulling the inner needle 11 out of the outer needle 6 of the double needle 1, the preparation holder 3 in condition shown in FIG. 1b is fitted in the fitting hole 10 of the outer needle.

Figure 3B:
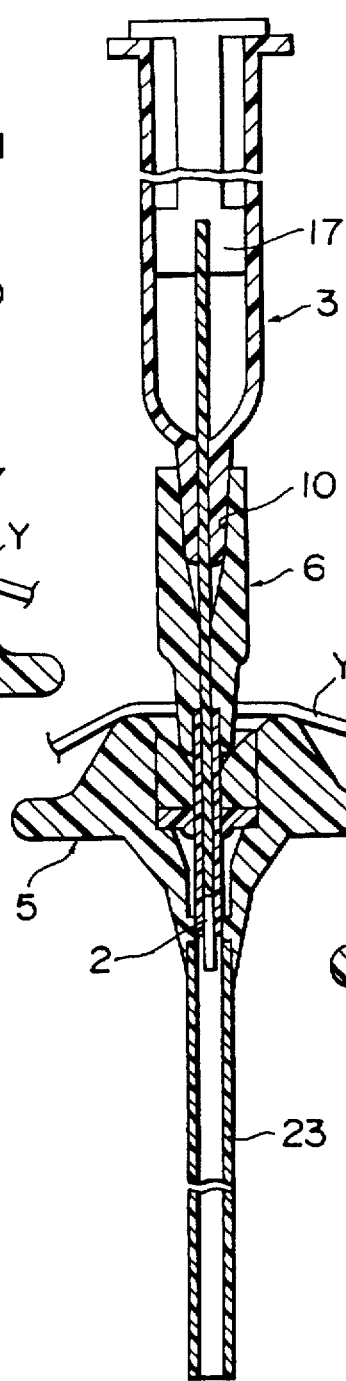
Figure 3C:
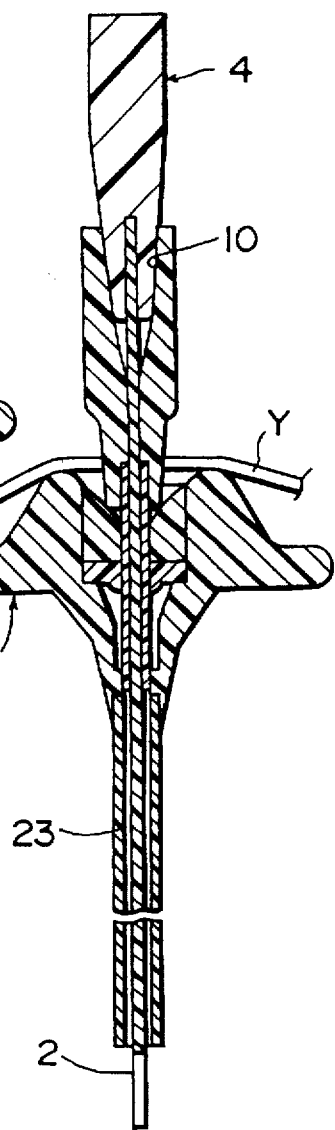

Next, the plunger 17 of the preparation holder 3 is pushed into the outer needle to load the preparation into the outer needle 6 (FIG. 3b). After pulling the preparation holder 3 out of the outer needle 6, the plunger 4 is put in the fitting hole 10 of the outer needle 6 and pushed thereinto step by step, whereby the preparation 2 is moved in the guide tube 23 of the preparation-introducing guide 5 toward the site of administration in the brain and administered thereto by pushing the plunger 4 to the end (FIG. 3c).

Finally, the outer needle 6 is pulled out of the preparation-introducing guide 5 along with the plunger 4 or after removal of the plunger 4. As soon as the outer needle 6 is pulled out of the elastic member 21 of the preparation-introducing guide 5, the bore, which has been formed in the elastic member 21 by penetration of the outer needle 6, is pushed and closed by the elasticity of the elastic member 21. Accordingly, it prevents cerebrospinal fluid from backflow.

When a new preparation should be administered to the brain after the lapse of a certain period of time, it is sufficient to carry out the above procedures after cutting a part of the scalp, with which the preparation-introducing guide 5 implanted in the head is covered, by means of a surgical knife or the like, and inserting a double needle 1 of a new intracerebral preparation-administering equipment into the preparation-introducing guide 5.

Accordingly, the use of the intracerebral preparation-administering equipment of the present invention makes it possible to administer the preparations to the predetermined site of administration in the brain repeatedly by simple procedures without performing surgical operations, provided that once a preparation-introducing guide is implanted in the head. Further, if a preparation sustaining its drug efficacy for a long time, for example, a sustained release preparation is used as the preparation, there is no need to perform the administration-at frequent intervals. In addition, it will save much time and trouble required for the medical treatment and makes it possible to reduce the risk of infection as well as the physical and mental pains and economical burden of the patient.

In the foregoing embodiment, the preparation 2 is loaded into the preparation-introducing guide 5 by the preparation holder 3, but it is not necessarily required to use the preparation holder 3. The preparation may be loaded in the preparation-introducing guide 5 by placing an aseptically packaged preparation 2 in the fitting hole 10 of the outer needle 6 with a pair of tweezers and then pushing it into the preparation-introducing guide 5 by the plunger 4.

Further, in case of that a semisolid preparation is to be used as the preparation, the administration may be carried out by use of a tube having such an outside diameter that it may pass through the preparation-introducing guide. Furthermore, it is also possible to administer a liquid-like preparation to the brain by encapsulating it in a capsule or film which dissolves quickly within the brain.

Figure 4A:
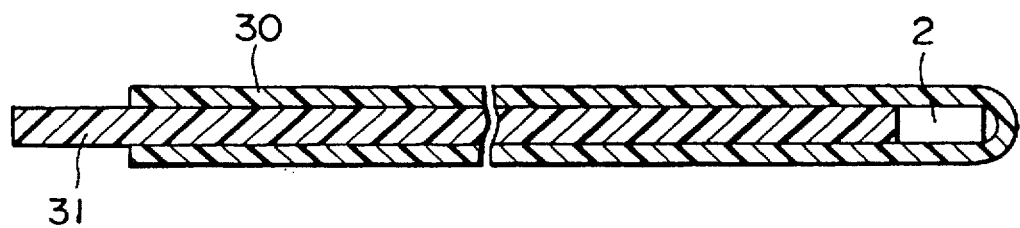
FIGS. 4(a) and 4(b) are sectional views of an intracerebral preparation-administering equipment illustrating another embodiment of the present invention.
Figure 4B:
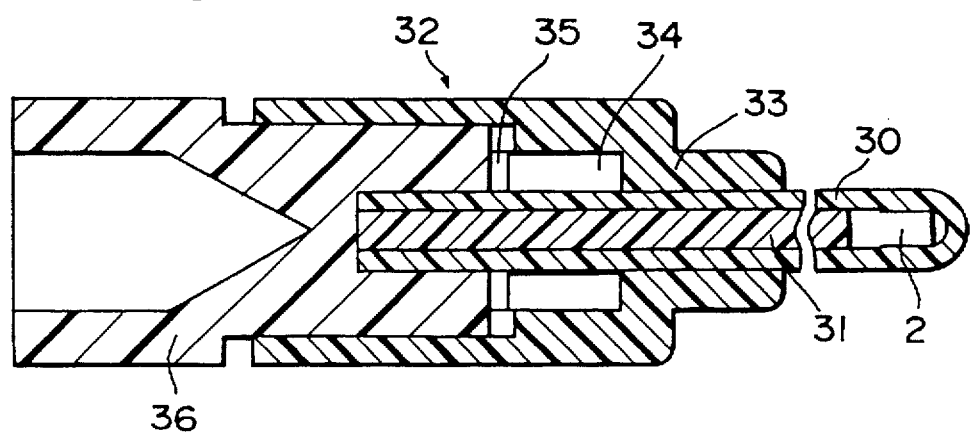

FIGS. 4(a) and 4(b) shows another embodiment of the present invention, which is so designed as to make it possible to administer a new preparation to the brain after removal of a residual preparation when it is required to administer the preparation repeatedly because of the facts that the preparation does not disintegrate, dissolve, or decompose in the brain. This intracerebral preparation-administering equipment comprises a preparation-retaining member 30 containing a preparation 2 therein, a push rod 31 removably inserted in the preparation-retaining member 30, and a holder 32 holding them as an integral part thereof.

The preparation-retaining member 30 is composed of a ultrafiltration membrane tube of a material with a good biocompatibility, for example, a hollow fiber membrane of polyether sulphone and closed at a distal end. The preparation-retaining member may be a tube of ethylene hexafluoride, perfluoroethylene or ethylene tetrafluoride, having perforations smaller than the preparation. The preparation-retaining member 30 may be formed into any size, but its size is usually determined to 0.5–1.0 mm in inside diameter and 0.8–1.5 mm in outside diameter. In order to administer the preparation to a desired site, it is preferred to prepare the preparation-retaining member 30 with a somewhat longer than the required length so that the preparation-retaining member can be adjusted in length by cutting it, for example, at a position illustrated in FIG. 4a by a broken line, together with the push rod 31 by scissors as occasion demands.

The push rod 31 is made of a flexible material such as nylon, silicone, polytetrafluoroethylene, polyacetal, ethylene tetrafluoride and the like in the form of a rod with a diameter equal to or slightly smaller than the inside diameter of the preparation-retaining member 30, and adjusted to be suitable for keeping the preparation 2 loaded in the preparation-retaining member 30 at a distal end thereof. The push rod is made of a material softer than that of the flexible guide tube since it is required to move it back and forth together with the preparation-retaining member 30 within the flexible guide tube 23 along the entire length thereof without causing displacement of the flexible guide tube 23.

The holder 32 is composed of a tubular holder body 33, a holding ring 34 of an elastic material such as silicone rubber, a pressure ring 35 of a relatively hard material such as silicone resin, and a tubular fixing member 36. The preparation-retaining member 30, which has been previously equipped with the preparation 2 and the push rod 31, is inserted into the holding ring 34 and pressure ring 35, and then inserted from the distal end thereof into the body 33. The fixing member 36 is then screwed in a threaded hole of the proximal end of the body 33 to press the holding ring 34 toward the body, whereby the holding ring 34 is compressed and deformed to fix the preparation-retaining member 30 in place (cf. FIG. 4b).

Figure 5:
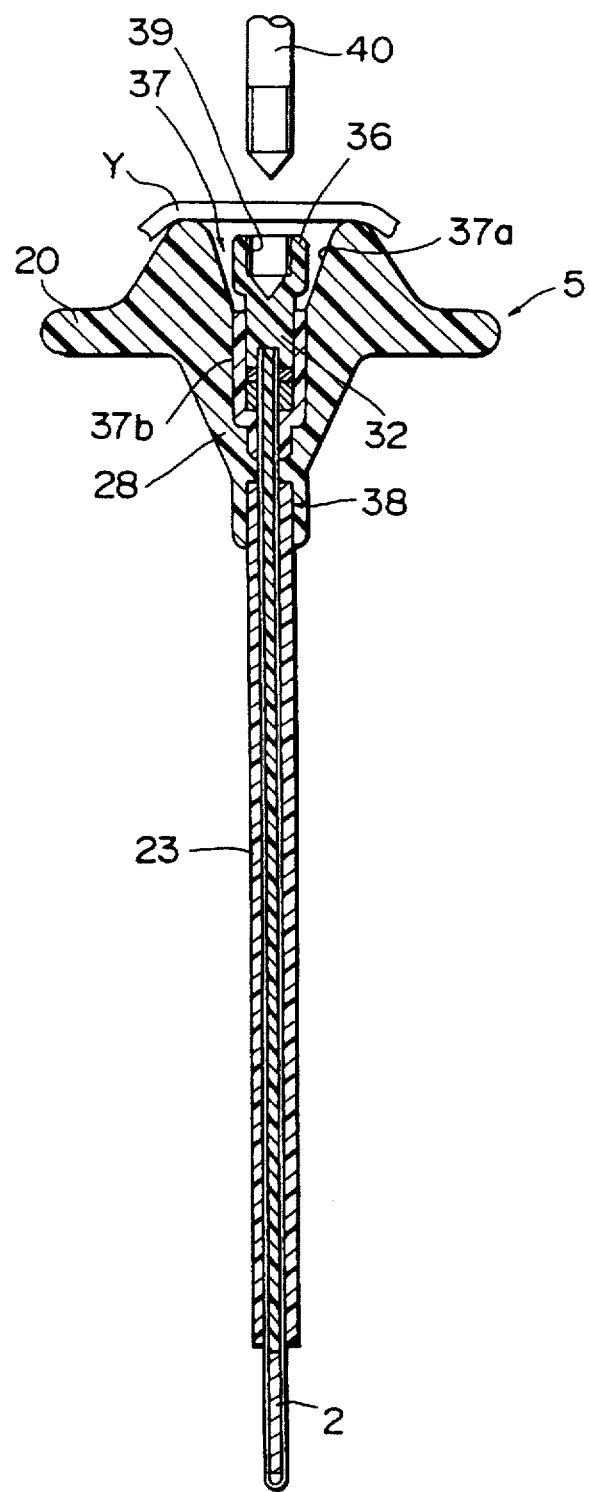
FIG. 5 is an explanatory diagram illustrating the condition of the intracerebral preparation-administering equipment of FIG. 4 that is in use.

The intracerebral preparation-administering equipment with the above structure is used in combination with a preparation-introducing guide 5 previously implanted in the head, in the same manner as that of the embodiment of FIG. 1. In this case, the preparation-introducing guide 5 is, as shown in FIG. 5, composed of a guide body 20 of silicone resin and a flexible guide tube 23. The guide body 20 has a guide hole 37 including a tapered portion 37a and a cylindrical portion 37b joined thereto, and the cylindrical portion 37b of the guide hole 37 is communicated with the guide tube-mounting hole 38 which passes through the tapered projection 28 formed as an integral part of the lower portion of the guide body 20. Within the mounting hole 38, the flexible guide tube 23 is arranged coaxially with the guide hole 37.

In use, the preparation-retaining member 30, which has been previously provided with the preparation 2 and the push rod 31, is cut at a point corresponding to a length up to the site of administration. This length is determined by taking an X-ray photograph of the preparation-introducing guide 5 which was previously fixed in the head of the patient by surgical operation. Then, the preparation-retaining member 30 is fixed in the holder 32 to complete the intracerebral preparation-administering equipment. The preparation-retaining member 30 is inserted into the guide hole 37 of the preparation-introducing guide 5 through the scalp Y cut with a surgical knife until the holder 32 is received into the guide hole 37 of the preparation-introducing guide 5, thereby the preparation 2 held in the preparation-retaining member 30 is put in place in the brain and the guide hole of the preparation-introducing guide 5 is closed by the holder 32 to prevent the backflow of the cerebrospinal fluid. In order to make a sure seal between the holder 32 and the guide hole 37, it may be possible to provide a seal ring between the holder body 33 and fixing member 36.

By leaving the thus introduced preparation-administering equipment as it is, the preparation 2 in the preparation-retaining member dissolves gradually in the fluid infiltrating into the ultrafiltration tube constituting the preparation-retaining member 30, and is then administered to the site of administration in the brain by osmosis. After leaving intracerebral preparation-administering equipment for a certain period of time, the scalp Y is cut open with a surgical knife so that the preparation-retaining member 30 may pass through the opening. Then, the preparation-retaining member 30 is pulled out of the preparation-introducing guide 5 so as to complete the administration, using an extracting metal part 40 which has a threaded lower end adapted to be screwed into the threaded bore 39 of a head portion of the fixing member 36 of the holder 32. This is done by inserting the extracting metal part 40 into the preparation-introducing guide 5, screwing it into the threaded bore 39 of the head portion of the holder 32, and then extracting the extracting metal part 40 from the preparation-introducing guide 5. If necessary, a holder 32 provided with a new preparation-retaining member 30 containing a preparation may be inserted into the preparation-introducing guide 5.

With the intracerebral preparation-administrating equipment of the above embodiment, it is possible to administer the preparation to the site of administration surely. Further, if the release of the drug has been completed or if the administration of the preparation is to be stopped, the residue or residual preparation can be collected by extracting the preparation-retaining member from the site of administration.

Figure 6:
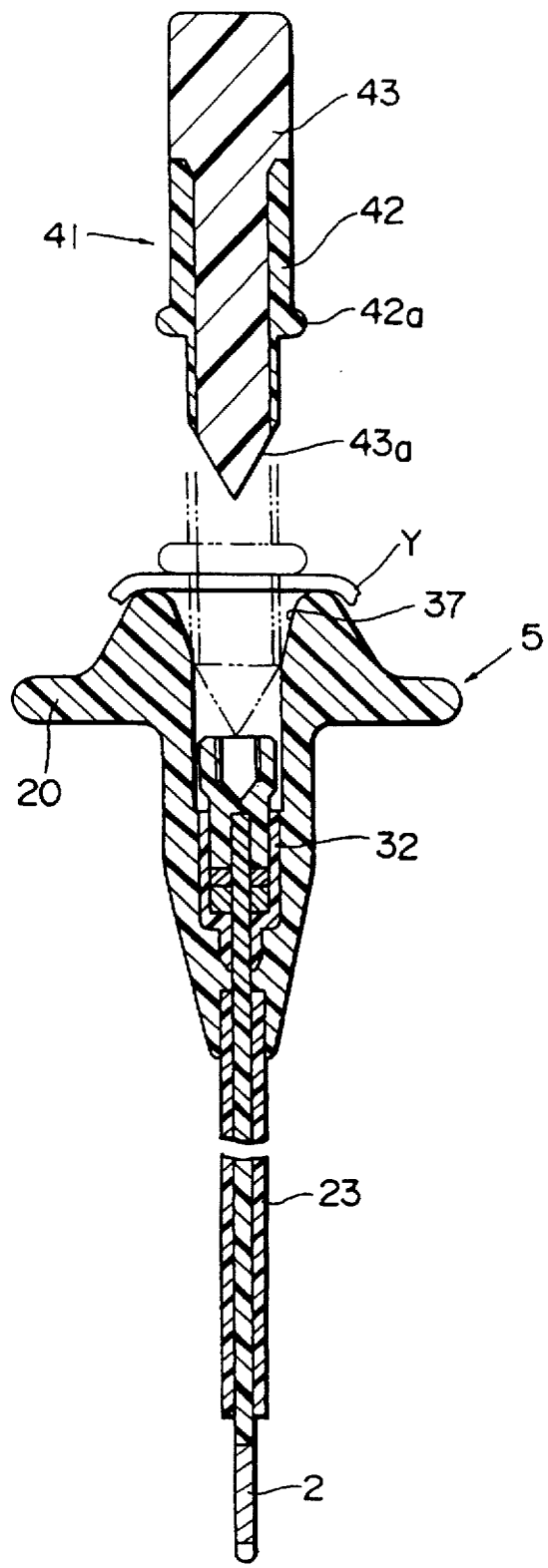
FIG. 6 is an explanatory diagram illustrating still another embodiment of an intracerebral preparation administering-equipment of the present invention in use.

FIG. 6 shows still another embodiment of the intracerebral preparation-administering equipment according to the present invention, which enables to perform intracerebral administration of preparations repeatedly, when the preparation does not or insufficiently disintegrate, dissolve, or decompose in the brain, by administer a new preparation to the brain after taking a residual preparation out of the site of administration, like the embodiment of FIG. 4. This intracerebral preparation-administering equipment further comprises a double needle 41 in addition to parts of the administering equipment shown in FIG. 4. The double needle 41 is composed of a cylindrical outer barrel 42 and an inner needle 43 removably arranged in the outer barrel 42. The inner needle 43 is tapered at a distal end 43a thereof and adapted to be removably inserted into the guide hole 37 of the preparation-introducing guide 5.

In use, the preparation-retaining member 30, into which a preparation 2 and a push rod 31 have been previously loaded, is cut at a point corresponding to a length up to the site of administration and then fixed to the holder 32 to assemble a preparation-retaining member set. Then, the scalp Y is cut with a surgical knife at an area over the previously implanted preparation-introducing guide 5, and the double needle 41 is inserted into the guide hole 37 of the preparation-introducing guide 5 through the scalp. After the double needle 41 is put in place by inserting it until the flanged portion 42a of the outer barrel 42 comes into contact with the scalp as indicated by a broken line in FIG. 6, the inner needle 43 is pulled out of the outer barrel 42 and then the preparation-retaining member 30 is inserted into the preparation-introducing guide 5 through the outer barrel 42 until the holder 32 is received in the guide hole 37 of the preparation-introducing guide 5, thereby the preparation is held in place in the brain. After this, the outer barrel 42 is removed from the preparation-introducing guide 5 and the scalp is stitched with a surgical needle to complete the administration procedures.

When the preparation-retaining member 30 has to be taken out of the preparation-introducing guide 5 after leaving it for a certain time or a certain period of time, this may be done by cutting the scalp open with a surgical knife so that the preparation-retaining member holder 32 may pass therethrough, inserting a double needle 41 into the preparation-introducing guide 5 until the flanged portion 42a of the outer barrel 42 comes into contact with the scalp, pulling the inner needle 43 out of the outer barrel 42, screwing the extracting metal part 40 in the preparation-retaining member holder 32 through the outer barrel 42, and then pulling them out of the preparation-introducing guide 5. If necessary, a new preparation-retaining member set with a new preparation may be inserted into the preparation-introducing guide 5.

Even in this embodiment, the intracerebral preparation-administrating equipment makes it possible to administer the preparation to the desired site surely, without performing surgical operations, when used in combination with the preparation-introducing guide previously implanted in the head. Further, if the release of the drug has been completed or if the administration of the preparation is to be stopped, the residue or preparation can be collected by extracting the preparation-retaining member from the preparation-introducing guide.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. Equipment for intracerebral administration of preparations comprising:

a preparation-introducing guide implantable in the head of a patient;

preparation-administrating means for inserting a solid or semi-solid preparation through the preparation-introducing guide;

a flexible plunger insertable into and readily removable from the preparation-administrating means;

said preparation-introducing guide comprising a guide body with a guide hole passing therethrough for introducing preparations, the guide body including an upwardly protruded head portion which causes a slight swelling of a scalp of the patient and a downwardly protruded tapered projection, backflow check means for preventing a cerebrospinal fluid from backflowing when said preparation-introducing guide is implanted in the head of a patient, said backflow check means being arranged in the guide hole of said guide body to close said guide hole; and a flexible guide tube connected to the downwardly protruded tapered projection of said guide body and communicated with said guide hole to introduce the preparation into a site of administration, the preparation-administrating means including a hollow needle at one end and an inner needle removably inserted into said hollow needle, the hollow needle being insertable into and readily removable from the preparation-introducing guide, the flexible plunger being inserted into said preparation-administrating means after removing said inner needle from the hollow needle and loading a preparation into the preparation-administrating means to push the preparation to a site of administration through said preparation-introducing guide.

2. The equipment for intracerebral administration of preparations claimed in claim 1, wherein said preparation-administrating means further includes a preparation holder comprising a preparation holder body and a loading plunger, the preparation holder body holding a solid or semi-solid preparation therein and being detachably mounted to the hollow needle after removing the inner needle from the hollow needle, the preparation-loading plunger being detachably mounted in said holder body and loading the preparation into the preparation-introducing guide through the hollow needle.

3. The equipment for intracerebral administration of preparations claimed in claim 1, wherein at least the hollow needle is insertable through the backflow check means.

4. The equipment for intracerebral administration of preparations claimed in claim 3, wherein the backflow check means has a diameter slightly greater than the guide hole such the backflow check means is press-fitted in the guide hole, at least the hollow needle being insertable through the backflow check means to form a bore therein such that the preparation is passed therethrough to the site of administration, the backflow check means closing the bore upon withdrawal of the hollow needle to thereby close the guide hole and seal the preparation-introducing guide from ambient environment.

5. The equipment for intracerebral administration of preparations claimed in claim 3, wherein the backflow check means is initially without any openings to thereby close the guide hole and seal the preparation-introducing guide from ambient environment.

6. The equipment for intracerebral administration of preparations claimed in claim 1, wherein the hollow needle of the preparation-administrating means has one of the inner needle, a preparation holder and the flexible plunger inserted therein, with the inner needle inserted into the hollow needle, the preparation-administering means initially engages the preparation-introducing guide, a preparation being inserted into the preparation-introducing guide when the preparation holder is inserted into the hollow needle, the preparation-introducing guide having a preparation-administering plunger for pushing the preparation from the preparation holder into and out of the hollow needle, and the flexible plunger being inserted into the hollow needle to push the preparation through the preparation-introduction guide, the inner needle, the preparation holder and the flexible plunger all only being sequentially insertable into the hollow needle and all being readily detachable from the hollow needle.

7. Equipment for intracerebral administration of solid or semi-solid preparations, for use in combination comprising:

a preparation-introducing guide implantable in the head of a patient;

preparation-retaining means having a solid or semi-solid preparation therein and being held in the preparation-introducing guide implanted in the head of a patient to administer a preparation, said preparation-introducing guide comprising a guide body, backflow check means for preventing a cerebrospinal fluid from backflowing, and guide tube means for guiding the preparation introduced into said guide hole to an objective site in a brain, said guide body having a guide hole passing therethrough for introducing preparations and including an upwardly protruded head portion which causes a slight swelling of a scalp of the patient and a downwardly protruded tapered projection, said guide hole including a tapered guide hole and a cylindrical guide hole communicated therewith, said backflow check means being arranged in the cylindrical guide hole of the guide body to close said guide hole when said preparation-introducing guide is implanted in the head of a patient, the guide tube means being a flexible guide tube inserted in the downwardly protruded tapered projection of the guide body and communicated with the guide hole to introduce the preparation into a site of administration;

said preparation-retaining means comprising a tubular preparation-retaining member having a preparation therein, the tubular preparation-retaining member being freely movable within the flexible guide tube of said preparation-introducing guide, the preparation-retaining means further includes a needle member for introducing the tubular preparation-retaining member into the preparation-introducing guide; and a holder for holding said preparation-retaining member, said holder surrounding an end of the preparation-retaining member and being insertable into and fixable in the guide hole of said preparation-introducing guide, the holder constituting the backflow check means when inserted in said guide hole of said introducing guide.

8. The equipment for intracerebral administration of preparations claimed in claim 7, wherein said needle member has a double needle structure composed of an outer tube and an inner needle, said outer tube having an inside diameter through which said holder with preparation-retaining means may be passed.

9. The equipment for intracerebral administration of preparations claimed in claim 7, wherein said preparation-retaining means has a structure which permits diffusion and release of a drug contained in the preparation held therein.

10. The equipment for intracerebral administration of preparations claimed in claim 7, wherein the tubular preparation-retaining member is composed of a ultrafiltration membrane.

11. The equipment for intracerebral administration of preparations claimed in claim 7, further including a slender push rod of a flexible material removably inserted into the tubular preparation-retaining member.

12. The equipment for intracerebral administration of preparations claimed in claim 7, wherein said backflow check means is an elastic backflow check member press-fitted in said guide hole to close the guide hole, said backflow check member being fixed by a cylindrical pressure member fitted in said guide hole.

13. The equipment for intracerebral administration of preparations claimed in claim 7, wherein the holder comprises a holder body, at least one ring and a fixing member, the tubular preparation-retaining member extends from a forward end of the holder body, the at least one ring engages the tubular preparation-retaining member inside the holder body and the fixing member presses the at least one holding ring toward the forward end of the holder body to hold the tubular preparation-retaining member within the holder body.

14. The equipment for intracerebral administration of preparations claimed in claim 7, wherein the backflow check means has a diameter slightly greater than the guide hole such the backflow check means is press-fitted in the guide hole, the needle being insertable through the backflow check means to form a bore therein such that the preparation is passed therethrough to the site of administration, the backflow check means closing the bore upon withdrawal of the needle to thereby close the guide hole and seal the guide tube from ambient environment.

15. The equipment for intracerebral administration of preparations, claimed in claim 7, wherein the backflow check means is initially without any openings to thereby close the guide hole and seal the guide tube from ambient environment.

16. The equipment for intracerebral administration of preparations claimed in claim 7, wherein said holder is composed of a tubular holder body, a holding ring, a pressure ring of a relatively hard material, and a tubular fixing member.

17. The equipment for intracerebral administration of preparations claimed in claim 7, further comprising a push rod removably insertable into the tubular preparation-retaining member and wherein said tubular preparation-retaining member is composed of a ultrafiltration membrane of a good biocompatible material, and wherein said push rod is of a flexible material softer than that of the flexible guide.

18. The equipment for intracerebral administration of preparations claimed in claim 7, wherein the preparation in the tubular preparation-retaining member is at an end of the member opposite to the end surrounded by the holder.

19. The equipment for intracerebral administration of preparations claimed in claim 18, wherein the tubular preparation-retaining member is insertable into and through the guide to position the preparation in the end of the tubular preparation-retaining member outside the guide adjacent to the objective site in the brain.

* * * * *

UNITED STATES PATENT AND TRADEMARK OFFICE
CERTIFICATE OF CORRECTION

PATENT NO.   : 5,800,390
DATED        : September 1, 1998
INVENTOR(S)  : Toru Hayakawa, et. al.

It is certified that error appears in the above-identified patent and that said Letters Patent is hereby corrected as shown below:

Title page, item [73] Assignee: delete the second name, "Koken Co., Ltd., Tokyo" and insert -- Sumitomo Pharmaceuticals Company, Limited, Osaka, Japan--

Signed and Sealed this

Twenty-sixth Day of December, 2000

Attest:

Q. TODD DICKINSON

Attesting Officer

Director of Patents and Trademarks